(12) United States Patent
Labyed

(10) Patent No.: US 11,553,901 B2
(45) Date of Patent: Jan. 17, 2023

(54) LIVER DISEASE ACTIVITY ESTIMATION WITH ULTRASOUND MEDICAL IMAGING

(71) Applicant: Siemens Medical Solutions USA, Inc., Malvern, PA (US)

(72) Inventor: Yassin Labyed, Maple Valley, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 240 days.

(21) Appl. No.: 16/816,351

(22) Filed: Mar. 12, 2020

(65) Prior Publication Data

US 2020/0205786 A1 Jul. 2, 2020

Related U.S. Application Data

(63) Continuation-in-part of application No. 15/716,444, filed on Sep. 26, 2017.

(60) Provisional application No. 62/482,606, filed on Apr. 6, 2017.

(51) Int. Cl.
*A61B 8/08* (2006.01)
*A61B 8/00* (2006.01)

(52) U.S. Cl.
CPC .............. *A61B 8/5223* (2013.01); *A61B 8/08* (2013.01); *A61B 8/463* (2013.01); *A61B 8/481* (2013.01); *A61B 8/485* (2013.01); *A61B 8/486* (2013.01); *A61B 8/488* (2013.01); *A61B 8/5246* (2013.01)

(58) Field of Classification Search
CPC ......... A61B 8/5223; A61B 8/08; A61B 8/463; A61B 8/481; A61B 8/485; A61B 8/486; A61B 8/488; A61B 8/5246; A61B 8/54
See application file for complete search history.

(56) References Cited

U.S. PATENT DOCUMENTS

| | | | |
|---|---|---|---|
| 4,621,645 | A | 11/1986 | Flax |
| 4,664,123 | A | 5/1987 | Iinuma |
| 5,606,971 | A | 3/1997 | Sarvazyan |
| 5,810,731 | A | 9/1998 | Sarvazyan |

(Continued)

FOREIGN PATENT DOCUMENTS

| | | |
|---|---|---|
| WO | 2012158877 | 11/2012 |
| WO | 2012158877 A2 | 11/2012 |

(Continued)

OTHER PUBLICATIONS

Allen, Alina M., et al. "Novel multiparametric magnetic resonance elastography (MRE) protocol accurately predicts NAS score for NASH diagnosis." Journal of Hepatology 66.1 (2017): pp. 1-20.

(Continued)

*Primary Examiner* — Hien N Nguyen

(57) ABSTRACT

Ultrasound-based estimation of disease activity, such as for NAS or other activity index for NAFLD for liver disease, is provided. Ultrasound measures acoustic scatter and shear wave propagation parameters, such as measuring acoustic backscatter coefficient, shear wave velocity, and shear wave damping ratio. A score for the disease activity is determined from these scatter and shear wave propagation parameters. The physician may be assisted by relatively inexpensive and rapid ultrasound as compared to biopsy or MRI based scoring in scoring activity of a disease, such as NAFLD. Ultrasound imaging is more readily available and less expensive and MRI, and is non-invasive.

17 Claims, 3 Drawing Sheets

(56) References Cited

U.S. PATENT DOCUMENTS

| | | | |
|---|---|---|---|
| 6,770,033 | B1 | 8/2004 | Catheline et al. |
| 8,118,744 | B2 | 2/2012 | Palmeri |
| 8,961,418 | B2 | 2/2015 | Fan |
| 2002/0161300 | A1 | 10/2002 | Hoff et al. |
| 2006/0079773 | A1 | 4/2006 | Mourad et al. |
| 2008/0249408 | A1 | 10/2008 | Palmeri et al. |
| 2010/0016718 | A1 | 1/2010 | Fan |
| 2014/0276058 | A1 | 9/2014 | Fan et al. |
| 2014/0316267 | A1 | 10/2014 | Barry et al. |
| 2016/0302769 | A1 | 10/2016 | Labyed |
| 2018/0140219 | A1 | 5/2018 | Yin |
| 2018/0228463 | A1 | 8/2018 | Shamdasani et al. |

FOREIGN PATENT DOCUMENTS

| | | |
|---|---|---|
| WO | 2013017105 | 2/2013 |
| WO | 2013017105 A1 | 2/2013 |
| WO | 2013025798 | 2/2013 |
| WO | 2013025798 A1 | 2/2013 |

OTHER PUBLICATIONS

Allen, Alina M., et al. "The Role of Three-Dimensional Magnetic Resonance Elastography in the Diagnosis of Nonalcoholic Steatohepatitis in Obese Patients Undergoing Bariatric Surgery." Hepatology 71.2 (2020): 510-521.

Yin, Ziying, et al. "Prediction of nonalcoholic fatty liver disease (NAFLD) activity score (NAS) with multiparametric hepatic magnetic resonance imaging and elastography." European radiology 29.11 (2019): 5823-5831.

Chen, Jian-Feng, Ernest L. Madsen, and James A. Zagzebski. "A method for determination of frequency-dependent effective scatterer number density." The Journal of the Acoustical Society of America 95.1 (1994): 77-85.

Ghoshal, Goutam, et al. "Ex vivo study of quantitative ultrasound parameters in fatty rabbit livers." Ultrasound in medicine & biology 38.12 (2012): 2238-2248.

Hruska, David P., and Michael L. Oelze. "Improved parameter estimates based on the homodyned K distribution." IEEE transactions on ultrasonics, ferroelectrics, and frequency control 56.11 (2009).

Insana, Michael F., et al. "Describing small-scale structure in random media using pulse-echo ultrasound." The Journal of the Acoustical Society of America 87.1 (1990): 179-192.

Labyed, Yassin, and Timothy A. Bigelow. "A theoretical comparison of attenuation measurement techniques from backscattered ultrasound echoes." The Journal of the Acoustical Society of America 129.4 (2011): 2316-2324.

Labyed, Yassin, and Timothy A. Bigelow. "Estimating the total ultrasound attenuation along the propagation path by using a reference phantom." The Journal of the Acoustical Society of America 128.5 (2010): 3232-3238.

Lizzi, F. L. "Ultrasonic scatterer-property images of the eye and prostate." Ultrasonics Symposium, 1997. Proceedings., 1997 IEEE. vol. 2. IEEE, 1997.

Lizzi, F. L., et al. "Theoretical framework for spectrum analysis in ultrasonic tissue characterization." The Journal of the Acoustical Society of America 73.4 (1983): 1366-1373.

Lizzi, F. L., et al. "Ultrasonic spectrum analysis for tissue evaluation." Pattern Recognition Letters 24.4 (2003): 637-658.

Oelze, Michael L., and William D. O'Brien Jr. "Method of improved scatterer size estimation and application to parametric imaging using ultrasound." The Journal of the Acoustical Society of America 112.6 (2002): 3053-3063.

Sasso, Magali, et al. "Controlled attenuation parameter (CAP): a novel VCTE™ guided ultrasonic attenuation measurement for the evaluation of hepatic steatosis: preliminary study and validation in a cohort of patients with chronic liver disease from various causes." Ultrasound in medicine & biology 36.11 (2010): 1825-1835.

Schwenzer, Nina F., et al. "Non-invasive assessment and quantification of liver steatosis by ultrasound, computed tomography and magnetic resonance." Journal of hepatology 51.3 (2009): 433-445.

Barry, et al., "SHear Wave Dispersion Measures Liver Steatosis," Ultrasound in Med. & Biol., vol. 38, No. 2, pp. 175-182, 2012.

Palmeri, et al., "Noninvasive evaluation of hepatic fibrosis using acoustic radiation force-based shear stiffness in patients with non-alcoholic fatty liver disease," Journal of Hepatology, Elsevier, Amsterdam NL, vol. 55, No. 3, Dec. 9, 2010, pp. 66-672.

Shen, et al. "Precise Tracing of impulsive Acoustic Radiation Force Induced Small displacements for Shear wave speed estimation," Ultrasonic Symposium 2011 ISEE Oct. 18, 2011; pp. 2402-2407.

Nightingale, Kathryn, "Acoustic Radiation Force Impulse Imaging: Ex Vivo and In Vivo Demonstration of Transient Shear Wave Propagation"; IEEE International Symposium on Biomedical Imaging; Proceedings; pp. 525-528.

Saishruthi Swaminathan "Logistic Regression—Detailed Overview" Towards Data Science. Mar. 15, 2018. pp. 1-13. https://towardsdatascience.com/logistic-regression-detailed-overview-46c4da4303bc.

Wikipedia "Logistic Regression" Retrieved Mar. 9, 2022. pp. 1-32. https://en.wikipedia.org/wiki/Logistic_regression.

LIVER DISEASE ACTIVITY ESTIMATION WITH ULTRASOUND MEDICAL IMAGING

RELATED APPLICATIONS

The present patent document is a continuation-in-part of U.S. patent application Ser. No. 15/716,444, filed Sep. 26, 2017, which claims the benefit of the filing date under 35 U.S.C. § 119(e) of Provisional U.S. Patent Application Ser. No. 62/482,606, filed Apr. 6, 2017. Both applications are hereby incorporated by reference.

BACKGROUND

The present embodiments relate to ultrasound imaging. A disease-related activity in tissue, such as liver, is measured using ultrasound.

Nonalcoholic fatty liver disease (NAFLD) is the most common liver disease in American adults and children. NAFLD is characterized by excess hepatic fat accumulation as well as hepatic fibrosis. Fat fraction may be measured as an indicator of NAFLD. Fat fraction in the liver or other tissues, such as breast tissue, and/or other tissue properties (e.g., degree of fibrosis) provide diagnostically useful information.

Over 25% of patients with NAFLD develop non-alcoholic steatohepatitis (NASH). NASH may progress to cirrhosis and hepatocellular carcinoma. A NAFLD activity score (NAS) is used to diagnose and monitor changes or level of NASH. NAS is provided from histologic evaluation of liver biopsies and is calculated as an unweighted sum of the observed steatosis, lobular inflammation, and ballooning scores.

Magnetic resonance imaging (MRI) may measure the proton density fat fraction (PDFF) as a biomarker of hepatic fat content. MRI may be used to further estimate NAS. However, MRI is not widely available and is expensive.

SUMMARY

By way of introduction, the preferred embodiments described below include methods, instructions, and systems for ultrasound-based estimation of disease activity, such as for NAS or other activity index for NAFLD. Ultrasound measures acoustic scatter and shear wave propagation parameters, such as measuring acoustic backscatter coefficient, shear wave velocity, and shear wave damping ratio. A score for the disease activity is determined from these scatter and shear wave propagation parameters. The physician may be assisted by relatively inexpensive and rapid ultrasound as compared to biopsy or MRI based scoring in scoring activity of a disease, such as NAFLD. Ultrasound is non-invasive, and more readily available and less expensive than MRI.

In a first aspect, a method is provided for non-alcoholic liver disease activity estimation with an ultrasound scanner. A first measure of scattering in tissue is generated from a scan of a patient by the ultrasound scanner. The first measure of scattering is a backscatter coefficient. Second and third measures of shear wave propagation in the tissue are generated from the scan of the patient by the ultrasound scanner. The second measure is a shear wave velocity, and the third measure is a shear wave damping ratio. A first value for an ultrasound-derived liver disease activity index is estimated from the backscatter coefficient, the shear wave velocity, and the shear wave damping ratio. An ultrasound image including an indication of the first value of the ultrasound-derived liver disease activity index as estimated is output.

In a second aspect, a system is provided for estimation of disease activity. A beamformer is configured to transmit and receive sequences of pulses in a patient with the transducer. The sequence of pulses is for a scatter parameter and for first and second shear wave parameters. An image processor is configured to generate a score for an index of the disease activity from a combination of the scatter parameter, the first shear wave parameter, and the second shear wave parameter. A display is configured to display the score for the index of the disease activity.

In a third aspect, a method is provided for liver disease activity estimation with an ultrasound system. The ultrasound system determines a plurality of scattering parameters of liver tissue of a patient. The ultrasound system determines a plurality of shear wave parameters of the liver tissue of the patient. A fat fraction is estimated from at least one of the scattering parameters. A level of the liver disease activity is estimated from the fat fraction and at least one of the shear wave parameters. The level of the liver disease is displayed.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Disease activity is estimated to assist with diagnosis, screening, monitoring, and/or predicting health conditions. For example, NAS or other liver disease activity is estimated. A score of an index is estimated using ultrasound, allowing for rapid, inexpensive, and non-invasive estimation of the disease activity. An ultrasound-derived NAFLD activity score is estimated, avoiding biopsy or MRI.

The disease activity may be estimated from measurements used in estimating tissue properties, such as liver fat fraction and/or estimates of the liver fat fraction. The measurements and estimation of fat fraction or other tissue properties is discussed below with respect to FIG. 1. The use of these measurements and/or tissue properties in estimating the disease activity is then discussed with respect to FIG. 3.

Regarding tissue property estimation, quantitative ultrasound (QUS) is used for screening, diagnosing, monitoring, and/or predicting health conditions. The complexity of human tissue may be measured using multiple QUS parameters for accurate characterization of that tissue. For example, liver fat fraction is estimated using a multi-parametric approach that combines quantitative parameters extracted from the received signals of different wave phenomena, such as scattering and attenuation of longitudinal waves, propagation and attenuation of shear waves, and/or propagation and attenuation of on-axis waves from acoustic radiation force impulse (ARFI).

In one embodiment, a tissue property (e.g., liver fat fraction) is estimated by transmitting and receiving a sequence of pulses to estimate scattering parameters, and by transmitting and receiving a sequence of pulses to obtain shear wave parameters. The estimation may also include transmitting and receiving a sequence of pulses to estimate parameters from axial displacements caused by acoustic radiation force impulses (ARFI). The QUS parameters are estimated and combined to estimate the tissue property. Other information may be included in the estimation of the tissue property, such as non-ultrasound data (e.g., blood biomarker).

Figure 1:
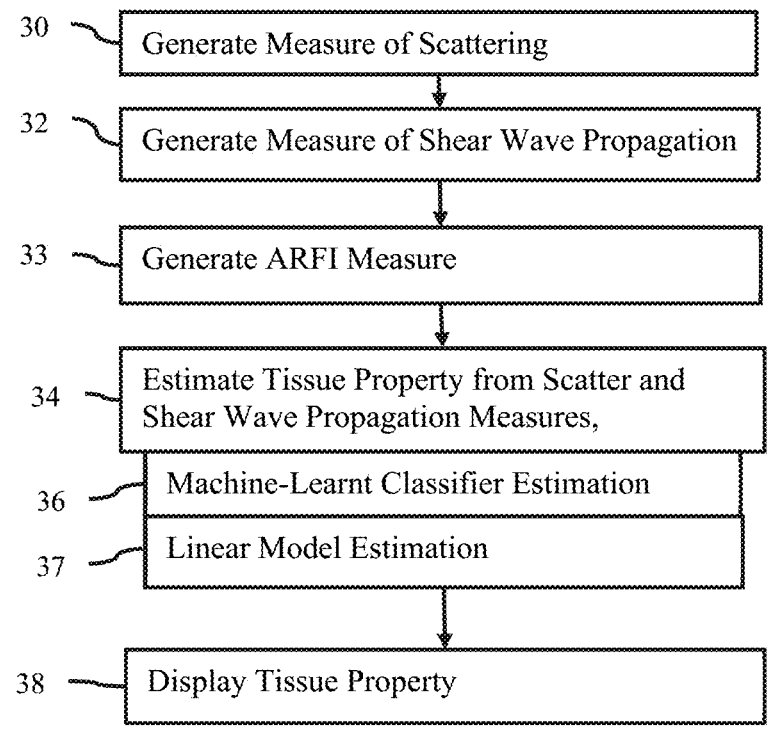
FIG. 1 is a flow chart diagram of one embodiment of a method for estimating a tissue property with ultrasound.

FIG. 1 shows a method for tissue property estimation with an ultrasound scanner or system. Tissue reactions to different types of waves or wave phenomena are measured. The combination of the measures of these different reactions is used to estimate the tissue property.

Figure 2:
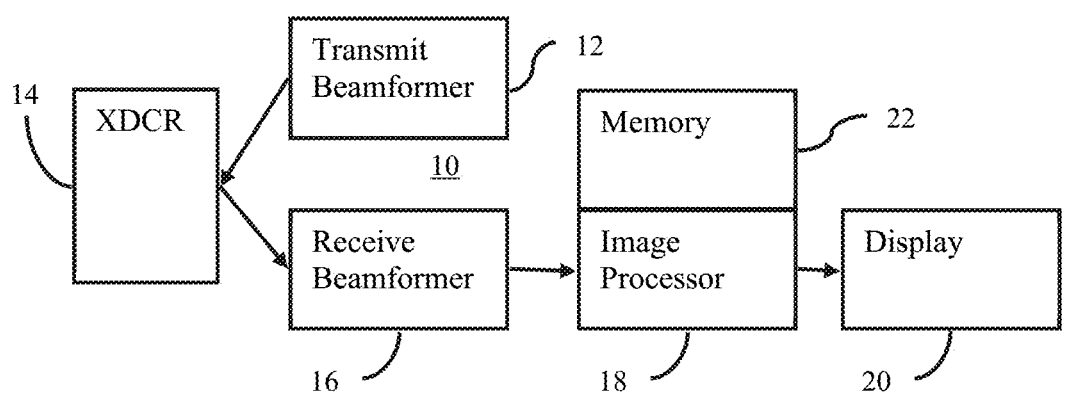
FIG. 2 is a block diagram of one embodiment of a system for estimating a tissue property with ultrasound.

The method is implemented by the system of FIG. 2 or a different system. A medical diagnostic ultrasound scanner performs the measurements by acoustically generating the waves and measuring the responses. An image processor of the scanner, computer, server, or other device estimates from the measurements. A display device, network, or memory is used to output the estimated tissue property.

Additional, different, or fewer acts may be provided. For example, acts 33 and/or 38 are not provided. As another example, acts 36 and 37 are alternatives or may be used together, such as averaging results from both. In another example, acts for configuring the ultrasound scanner and/or scanning are provided.

The acts are performed in the order described or shown (e.g., top to bottom or numerically), but may be performed in other orders. For example, acts 30, 32, and 33 are performed simultaneously, such as using the same transmit and receive pulses, or are performed in any order.

In act 30, an ultrasound scanner generates a measure of scattering in tissue from a scan of a patient. The measure of scatter measures a tissue response to a longitudinal wave transmitted from an ultrasound scanner. The scattering or echo of the longitudinal wave impinging on the tissue is measured.

Any measure of scatter may be used. Example scatter parameters include sound speed, sound dispersion, angular scattering coefficient (e.g., backscatter coefficient), frequency-dependent attenuation coefficient, attenuation coefficient slope, spectral slope of the normalized log-spectrum, spectral intercept of the normalized log-spectrum, spectral midband of the normalized log-spectrum, effective scatterer diameter, acoustic concentration, scatterer number density, mean scatterer spacing, nonlinearity parameter (B/A), and/or ratio of coherent to incoherent scattering.

More than one measure may be performed. For example, the ultrasound system determines values for two or more scattering parameters of the patient tissue. In one embodiment, the acoustic attenuation coefficient, backscatter coefficient, and/or spectral slope of a logarithm of the frequency-dependent backscatter coefficient are measured.

To measure the scatter, the ultrasound scanner scans the tissue with ultrasound. A sequence of transmit and receive events is performed to acquire the signals to estimate the quantitative ultrasound scatter parameters. In one embodiment, a one, two, or three-dimensional region is scanned by a B-mode sequence (e.g., transmit a broadband (e.g., 1-2 cycle) transmit beam and form one or more responsive receive beams). Any scan format may be used, such as linear, sector, or vector. The transmit and receive operations may be repeated for each scan line. Narrow band pulses (e.g., 3 or more cycles) may be transmitted and received at distinct center frequencies with or without overlapping spectra. Narrow band transmit pulses may be used in a single or in multiple transmit and receive events. The transmit pulses and corresponding receive beams may be formed at different steering angles, such as sampling a same location of tissue from different directions. Different steering may be performed just for transmit or just for receive. Different transmit beams may have different transmit powers and/or F numbers. The single transmit or multiple transmits may be focused, unfocused, or use a plane wave. Any scan sequence may be used.

Repetition with or without different transmit and/or receive settings may be used to measure the scatter once or to measure the scatter differently. Where multiple measures of the same scatter parameter are provided for a same location, the measures may be averaged or combined. Measures from different locations, such as adjacent locations or locations within a given range, may be averaged. For example, the measure of scatter is a frequency dependent measure averaged from multiple transmissions to a same location. Changes in the power spectra as a function of depth, angle, and/or frequency may be measured. As another example, estimates of the attenuation coefficient from different transmit and/or receive angles are averaged to reduce variance or used to quantify the angular dependence of attenuation.

In one embodiment, the scanning to measure is adaptive. The transmissions and/or receptions may be adaptive. For example, results of one measure are used to set the amplitude, angle, frequency, and/or F# for subsequent transmissions.

In one example, the attenuation coefficient is measured. The reference-phantom method is used, but other measures of the attenuation coefficient may be used. Acoustic energy has an exponential decay as a function of depth. A measure of acoustic intensity as a function of depth before or without depth gain correction is performed. To remove system effects, the measurement is calibrated based on measures of acoustic intensity as a function of depth in a phantom. The measurement may be subject to less noise by averaging over a one, two, or three-dimensional region. The beamformed samples or acoustic intensity may be converted to the frequency domain, and the calculation performed in the frequency domain.

In another example, the backscatter coefficient is measured. The acoustic attenuation is determined. This acoustic attenuation is used to determine a reference calibration. By calibrating for the acoustic attenuation, the scattered energy is provided as the backscatter coefficient. The calculation may be performed in the frequency domain, providing measures as a function of frequency.

The spectral slope of the logarithm of the frequency-dependent backscatter is measured from the backscatter coefficient. The log of the backscatter coefficient is determined as a function of the frequency. A line is fit (e.g., least squares) to the log of the backscatter as a function of frequency to determine the spectral slope.

In act 32, the ultrasound scanner generates a measure of shear wave propagation in the tissue from the scan of the patient. For shear wave imaging, an acoustic radiation force impulse (ARFI or pushing pulse) is transmitted to tissue. The impulse causes displacement of the tissue at a location, resulting in generation of a shear wave. The shear wave travels generally transversely to the transmit beam of the pushing pulse. By tracking tissue displacement at one or more laterally spaced locations, the shear wave passing those locations may be detected. The time for the shear wave to travel from the origin to the later location and the distance between the locations provides a shear wave speed.

Any shear wave parameter may be determined. For example, a shear wave speed or velocity in tissue is measured. Other shear wave parameters include angular and/or frequency-dependent shear wave speed, angular and frequency-dependent shear wave attenuation, angular and/or frequency-dependent storage modulus, angular and/or frequency-dependent loss modulus, viscosity, and/or angular and/or frequency-dependent acoustic absorption coefficient.

The acoustic absorption coefficient is from absorption of the acoustic pulse, not from absorption of the shear wave. The acoustic absorption is determined as $F \propto \alpha I/c$, where F is the radiation force, I is the intensity of ARFI push pulse, c is the acoustic sound speed, and $\alpha$ is the acoustic absorption coefficient.

To measure shear wave, a pushing pulse or ARFI is transmitted to a focal location in the tissue. A reference scan for a resting state tissue position is performed before the pushing pulse or after the tissue returns to a resting state. The change in position or displacement of tissue at one or more locations space from the focal location are measured over time. Tracking scans are repetitively performed. Using correlation or other measure of similarity, the axial, 2D, or 3D shift of tissue from a reference time compared to a current tracking time is determined. The time of the maximum displacement indicates the time of the shear wave. Other timing may be used, such as the beginning or end of displacement. The time for the shear wave to reach the tracking location and the distance from the tracking location to the focal location of the pushing pulse provides the shear wave velocity. Other approaches may be used, such as solving for shear wave velocity at multiple locations by determining a shift in displacement profile (displacement as a function of time) for different tracking locations or solving from displacements as a function of location.

The measurement of the shear wave parameters may be a function of frequency and/or angle. By transmitting pushing pulses in beams from different angles and/or at different frequencies, the measurement is repeated. Spatio-temporal displacement profiles are used in the time or frequency domain to determine the measure. The results from the different angles may be used to determine an angular dependent measure.

The shear wave parameter may be measured at different locations. The measurement may be based on tissue displacement to one or a single pushing pulse. The measurement may instead be based on tissue displacement to multiple pushing pulses. The measurement is repeated for different regions using different pushing pulses.

To measure the shear wave parameter, both pushing pulse and tracking transmissions occur. The displacements are measured by receiving acoustic response to the tracking transmissions and not the pushing pulse transmissions. The same scan used for measuring the scattering parameter may be used to measure the shear wave parameter. For example, the reference scan prior to transmitting the pushing pulse and used for tracking is used to measure the scatter. In other embodiments, the scan for the shear wave parameter uses different transmissions and/or receptions than for the scattering parameter. The scan for measurements is divided into separate sequences of transmit and receive events for the different measurements.

The pushing pulse has a relatively long duration as compared to the tracking pulses, such as tens, hundreds or thousands of cycles for the pushing pulse and one-to-three cycles for the tracking transmissions. Where repetition is provided, different focal locations, frequencies, angles, powers, and/or F numbers may be used for the pushing pulses.

The same measurement may be repeated for a same location and/or different locations. Different frequency, F number, angle, power, focal locations, and/or other differences may be used for any repetition. The resulting measures may be used together to determine another measure or may be combined, such as averaged to reduce noise.

The ultrasound scanner may adapt the scanning for the shear wave parameter measurement. For example, for an estimate of the attenuation coefficient of the shear wave, the push pulse adapts. The center frequency, duration, f-number, or other characteristic of the push pulse is changed for a later transmission. The focus is tighter or weaker. The displacement to create the shear wave is larger or lesser. As another example, for an estimate of the absorption coefficient with an ARFI push pulse, another push pulse is transmitted with a tighter focus or longer duration. The change may improve signal-to-noise ratio (SNR) and/or reduce variability in the measurements.

The adaptation is based on any information. For example, the displacement profile is compared to a reference or calibration profile. As another example, an amount of displacement of a maximum, mean, or median displacement is determined. The information may indicate a need for a stronger or higher intensity pushing pulse or may indicate that lesser intensity pushing pulses is needed, allowing for a shorter cool down time.

In act 33, the ultrasound scanner generates an ARFI measure of axial displacement of the tissue. An ARFI transmission causes tissue to displace along an axis or scan line of the transmit beam. Rather than tracking a shear wave, the tissue displacement along the axis caused by the ARFI or in response to a longitudinal wave generated by the ARFI is tracked over time.

Any ARFI measure may be used. For example, the attenuation of the longitudinal wave of the ARFI pulse may be estimated from displacements tracked at locations spaced from the focal point of the ARFI. The measures may be at the focal point or other locations along the axial scan line.

To measure, the ARFI is transmitted along a scan line. Tracking scans are performed after transmission of the ARFI. The acoustic echoes from the tracking transmissions along the scan line are received. The received data is correlated with a reference from prior to or after ARFI-caused displacements. The amount of displacement as a function of time, location, transmit angle, and/or transmit frequency is determined. The amount of maximum displacement, displacement as a function of depth, and/or displacement as a function of time is used to calculate the ARFI measure.

The same measurement may be performed at other times and/or locations. The results from the repetition may be used to derive yet another measure or may be averaged.

The transmissions may adapt, such as adapting an F number, frequency, duration, power, and/or angle. The adaption may be in response to any measure, such as a magnitude of a maximum displacement.

Other measures may be used. Response of tissue to different types of waves and/or scanning are measured. One or more measures of a same type are used. For a given measure, a single instance, average, or distribution (e.g., standard deviation over time, duration, frequency, angle, and/or space) are performed. Any number of the same or different types of measures may be performed.

In act 34, the ultrasound scanner or other image processor estimates the tissue property of the tissue of the patient from different measures. The measures from two or more different wave phenomena are used. The values of two or more measures are used to estimate the tissue property. For example, both a measure of scattering and a measure of shear wave propagation are used to estimate the tissue property. In another example, a measure of on-axis displacement (e.g., ARFI measure) is used with the measure of acoustic scattering and/or measure of shear wave propagation.

Other information may be used for estimating the tissue property. For example, clinical information for the patient is used. The clinical information may be the medical history, age, body-mass index, sex, fasting or not, blood pressure, diabetic or not, and/or a blood biomarker measure. Example blood biomarkers include alanine aminotransferase (ALT) level, aspartate aminotransferase (AST) level, and/or alkaline phosphatase (ALP) level. Any information about the patient may be included.

Any tissue property may be estimated. For example, the fat fraction of tissue is estimated. The fat fraction of the liver, breast, or other tissue is diagnostically useful. The fat fraction in a liver of the patient assists in diagnosis of NAFLD. Other diagnostically useful tissue properties include inflammation, density, fibrosis, and/or nephron characteristic (count and/or diameter). The tissue property is binary, such as existing or not, or is an estimate along a scale (i.e., level or magnitude of the tissue property). Only one tissue property is estimated in one embodiment. In other embodiments, two or more different tissue properties are estimated from the same or different measures.

Acts 36 and 37 represent two different embodiments for estimating in act 34. The different embodiments are alternatives. Other embodiments may be used. Both or multiple embodiments may be used, such as determining a value for a tissue property in two ways and then averaging the results or selecting the result most likely to be accurate.

The value of the tissue property is estimated. In the embodiment of act 36, a machine-learnt classifier estimates the tissue property. The machine-trained classifier provides a nonlinear model. Any machine learning and resulting machine-learnt classifier may be used. For example, a support vector machine, probabilistic boosting tree, Bayesian network, neural network, or other machine learning is used.

The machine learning learns from training data. The training data includes various examples, such as tens, hundreds, or thousands of samples, and the ground truth. The examples include the input data to be used, such as values for scattering and shear wave propagation parameters. The ground truth is the value for the tissue property of each example. In one embodiment, the machine learning is to learn to classify the fat fraction based on scattering and shear wave propagation parameters. The ground truth for the fat fraction is provided with a magnetic resonance (MR) scan providing proton density fat fraction (PDFF). The MR-PDFF provides a percentage of fat for a location or region. The percentage of fat is used as the ground truth so that the machine learning learns to classify the percentage of fat from input values for the ultrasound parameters. Other sources of ground truth may be used for a given tissue property, such as from biopsies, modeling, or other measurements.

In one embodiment, the machine learning trains a neural network. The neural network includes one or more convolution layers that learn a filter kernel to distinguish between the values of a tissue property. The machine training learns what weighted combination (e.g., convolution using learnt kernel) of input values indicates the output. The resulting machine-learnt classifier uses the input values to extract the distinguishing information and then classifies the tissue property based on the extracted information.

The training provides one or more matrices. The matrix or matrices relate the input information to the output class. Hierarchal training and a resulting classifier may be used. Different classifiers may be used for different tissue properties. Multiple classifiers may be used for a same tissue property and the results averaged or combined.

In the embodiment of act 37, a linear model is used instead of or in addition to a machine-learnt model. A predetermined or programmed function relates the input values to the output values. The function and/or weights used in the function may be determined experimentally. For example, the weights are obtained by a least square minimization using MR-PDFF values.

Any linear function may be used. For example, the value of the tissue property is estimated from one or more scatter parameters and one or more shear wave propagation parameters. Any combination of addition, subtraction, multiplication, or division may be used.

In one embodiment, two or more functions (e.g., weighted combinations of measures) are provided. One of the functions is selected based on the value of one of the parameters. For example, the ultrasound-derived fat fraction (UDFF) estimation includes two functions, represented as weighted combinations:

$$UDFF = aP_1 + bP_2 + cP_3 + \ldots d \text{ for } P_{i:min} < P_i < P_{i:max}$$

$$UDFF = \alpha P_1 + \beta P_2 + c\gamma + \ldots \delta \text{ for } P_{k:min} < P_k < P_{k:max}$$

where d and $\delta$ are constants, a, b, c, $\alpha$, and $\beta$ are weights, and P is a measure of a parameter. One parameter $P_{i,k}$ is used to determine which function to select. The possible functions include two or three other parameters and weights. Additional, different, or fewer numbers of functions, parameters in a function, weights, and/or constants may be used. Different selection criteria may be used. The selection parameter may be of one type and the weighted parameters of each function of another type. Alternatively, different types (e.g., scattering and shear wave propagation) are included as weighted parameters regardless of the type or types of parameters used for selection.

In one example, AC is the acoustic attenuation coefficient (e.g., a scattering parameter), BSC is the backscatter coefficient (e.g., a scattering parameter), and SS is the spectral slope of the logarithm of the frequency-dependent backscatter coefficient (e.g., also a scattering parameter). SWS is the shear wave speed (e.g., a shear wave propagation parameter). Two functions based on scattering parameters are used, where the function for a given estimation is selected based on the shear wave propagation parameter, as represented as:

$$UDFF = 55AC + 114BSC - 42 \text{ for } SWS < \frac{1.3 \text{ m}}{\text{s}}$$

$$UDFF = -3.8SS + 425BSC - 9.4 \text{ for } SWS > 1.3 \text{ m/s}$$

The weights and constants are based on minimizing a difference from the fat fraction provided by MR-PDFF. Expert selected or other weights and/or constants may be used.

In act 38, the ultrasound scanner or a display device displays the estimated tissue parameter. For example, an image of the fat fraction is generated. A value representing the estimated fat fraction is displayed on a screen. Alternatively or additionally, a graphic (e.g., curve or icon) representing the estimated fat fraction is displayed. Reference to a scale or other reference may be displayed. In other embodiments, the fat fraction as a function of location is displayed by color, brightness, hue, luminance, or other modulation of display values in a one, two, or three-dimensional representation. The tissue property may be mapped linearly or non-linearly to pixel color.

The tissue property is indicated alone or with other information. For example, shear wave imaging is performed. The shear wave velocity, modulus or other information determined from tissue reaction to a shear wave is displayed. Any shear imaging may be used. The displayed image represents shear wave information for the region of interest or the entire imaging region. For example, where shear velocity values are determined for all the grid points in a region of interest or field of view, the pixels of the display represent the shear wave velocities for that region. The display grid may be different from the scan grid and/or grid for which displacements are calculated.

The shear wave information is used for a color overlay or other modulation of display values. Color, brightness, luminance, hue, or other display characteristic is modulated as a function of the shear wave characteristic, such as the shear wave velocity. The image represents a two- or three-dimensional region of locations. The shear data is in a display format or may be scan converted into a display format. The shear data is color or gray scale data but may be data prior to mapping with gray scale or color scale. The information may be mapped linearly or non-linearly to the display values.

The image may include other data. For example, shear wave information is displayed over or with B-mode information. B-mode or other data representing tissue, fluid, or contrast agents in the same region may be included, such as displaying B-mode data for any locations with shear wave velocity below a threshold or with poor quality. The other data assists the user in determining the location of the shear information. In other embodiments, the shear wave characteristic is displayed as an image without other data. In yet other embodiments, the B-mode or other image information is provided without shear wave information.

The additional estimated value of the tissue property is displayed substantially simultaneously with the shear wave, B-mode, color or flow mode, M-mode, contrast agent mode, and/or other imaging. Substantially accounts for visual perception of the view. Displaying two images sequentially with sufficient frequency may allow the viewer to perceive the images as being displayed at a same time. The component measures used to estimate the tissue property may also be displayed, such as in a table.

Any format for substantially simultaneous display may be used. In one example, the shear wave or anatomy image is a two-dimensional image. The value of the tissue property is text, a graph, two-dimensional image, or other indicator of the values of the estimate. A cursor or other location selection may be positioned relative to the shear or anatomy image. The cursor indicates selection of a location. For example, the user selects a pixel associated with an interior region of a lesion, cyst, inclusion, or other structure. The tissue property for the selected location is then displayed as a value, a pointer along a scale, or other indication. In another example, the tissue property is indicated in a region of interest (sub-part of the field of view) or over the entire field of view.

In another embodiment, shear wave or B-mode and fat fraction images are displayed substantially simultaneously. For example, a dual-screen display is used. The shear wave image (e.g., shear wave velocity) and/or B-mode image are displayed in one area of the screen. The fat fraction as a function of location is displayed in another area of the screen. The user may view the different images on the screen for diagnosis. The additional information or indication of the tissue property helps the user diagnose the region.

In one embodiment, the tissue estimation is provided as a real-time number or quantitative image. Since the tissue parameters may be estimated quickly, the value of the tissue parameter is estimated and output within 1-3 seconds of starting the scanning. The tissue property may be estimated at different times, such as before, during and/or after treatment. The estimates from the different times are used to monitor progression of the disease and/or response to therapy. For example, a percent change in the value of the tissue property over time is calculated and output.

Figure 3:
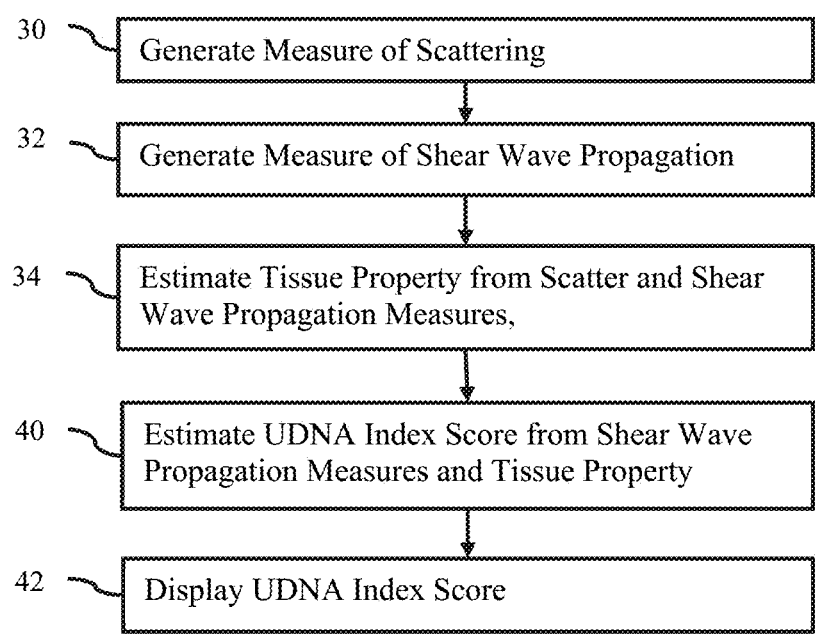
FIG. 3 is a flow chart diagram of one embodiment of a method for estimating disease activity, such as NAS, with ultrasound.

The tissue property and/or measurements used to derive tissue properties may be used in estimation of disease activity. FIG. 3 is a flow chart diagram of one embodiment of a method for disease activity estimation with an ultrasound system. For example, the method is for ultrasound-derived non-alcoholic liver disease activity estimation. An ultrasound scanner measures scatter and/or shear wave propagation in tissue of a patient for directly or indirectly estimating the disease activity.

For example, non-alcoholic fatty liver disease activity score (NAS) is predicted using quantitative ultrasound. NAS is predicted based on ultrasound estimates of tissue mechanical and acoustic properties. A model predicts NAS based on tissue mechanical and acoustic properties estimated using medical ultrasound. In one embodiment, an ultrasound system noninvasively obtains an ultrasound-derived NAFLD activity (UDNA) index as a predictor of NAS. The ultrasound system is configured to perform a pulse sequence for generating measures of scattering and shear wave propagation. The UDNA is determined using a model of at least three properties of the liver including the acoustic backscatter coefficient, the shear wave velocity, and the shear wave damping ratio.

Histological NAS is the sum of steatosis, lobular inflammation, and ballooning histologic scores but requires biopsy. In one embodiment, the proposed ultrasound-derived model pairs appropriate mechanical and acoustic properties with NAS features. The ultrasound-derived fat fraction, based on backscatter, attenuation, and/or sound speed, is used as a measure of steatosis grade. Shear wave damping ratio is used as a measure of inflammation, and shear wave speed is used as a measure of ballooning. Other ultrasound measurements may be used.

The method of FIG. 3 is implemented by the system of FIG. 2 or a different system. A medical diagnostic ultrasound scanner performs the measurements by acoustically generating the waves and measuring the responses. An image processor of the scanner, computer, server, or other device estimates from the measurements. A display device, network, or memory is used to output the estimated disease activity score.

Additional, different, or fewer acts may be provided. For example, acts 33 from FIG. 1 is included, such as using the ARFI measurement in the estimation of fat fraction or other tissue property. As another example, act 34 is not included, such as where the disease activity index score is estimated from the measurements without a separate estimation of the tissue property (e.g., fat fraction). In yet another example, act 38 is not provided. In another example, acts for configuring the ultrasound scanner and/or scanning are provided.

The acts are performed in the order described or shown (e.g., top to bottom or numerically), but may be performed in other orders. For example, acts 30 and 32 are performed simultaneously, such as using the same transmit and receive pulses, or are performed in any order.

In act 30, the ultrasound scanner generates one or more measures of scattering in tissue from an ultrasound scan of a patient. Any acoustic scatter parameters may be used, such as measurements of acoustic interaction with liver tissue. For example, the ultrasound scanner or system measures the backscatter coefficient, frequency-dependent backscatter coefficient, attenuation, sound speed, and/or any other of the scatter measurements discussed above for FIG. 1. The measure may be frequency dependent, such as averaged from multiple transmissions. Adaptive scanning may be used.

The measures of scattering may be used for estimating fat fraction, such as using acoustic backscatter (e.g., frequency dependent acoustic backscatter) and acoustic attenuation. The measures of scattering are alternatively or additionally used in estimation of the disease activity, such as using acoustic backscatter or frequency dependent acoustic backscatter.

In act 32, the ultrasound scanner generates one or more measures of shear wave propagation in the tissue from the ultrasound scan of the patient. Any shear wave propagation parameters may be used. For example, the shear wave velocity and shear wave damping ratio are used. Any of the shear wave propagation measurements discussed above for FIG. 1 may be used. The measurements are for an ARFI induced shear wave in the tissue of interest, such as the liver tissue, of the patient. Adaptive scanning may be used.

As discussed above for FIG. 1, the ultrasound scanning used for measuring scattering and for measuring shear wave propagation use the same or different transmit and receive events. For example, separate transmissions and receptions are used for measuring scattering than used to generate the shear wave and measure the tissue response to the shear wave.

In one embodiment, a shear wave damping ratio is generated. The ultrasound scanning is performed to measure tissue response to the shear wave in order to determine shear wave viscosity as a complex number, such as a ratio of the storage modulus to the loss modulus. This complex representation uses the real part of the viscosity as the storage modulus and the imaginary part of the viscosity as the loss modulus.

In one approach, spatio-temporal displacement measurements are acquired during shear wave propagation. These measurements are Fourier transformed into the frequency domain, such as using a fast Fourier transform, and used to determine the complex wave number. The log of a spectrum of displacement as a function of time may be determined for each of various locations subjected to a shear or other wave. Solving using the log as a function of location provides the complex wavenumber. Various viscoelastic parameters, such as loss modulus and storage modulus, are determined from the complex wavenumber. In one embodiment, the measurements to determine complex wavenumber, viscosity, or other damping ratio measurement disclosed in U.S. Published Patent Application No. 2016/0302769 are used.

As another approach, the shear wave attenuation and shear wave dispersion are measured. The dispersion is a change in shear wave speed or velocity as a function of frequency. The shear wave attenuation may also be measured as a function of frequency. For a given frequency or for a combination (e.g., average) from multiple frequencies, a phasor is generated based on the attenuation and dispersion values. This phasor is converted to a complex number, from which the real and imaginary parts are used as the damping ratio. Other measures of the damping ratio from tissue response to shear wave may be used.

The image processor estimates a value for an ultrasound-derived liver disease activity index from the backscatter coefficient, the shear wave velocity, and the shear wave damping ratio. Other measurements may be used. Non-ultrasound information may additionally be used, such as from the patient medical record.

The disease activity is estimated directly or indirectly from the measurements. For direct measurements, the measurements are input to a model, which outputs the estimate of the value of the disease activity in act 40. The score is directly estimated from the measurements. For indirect measurements, one or more types of measurements are used to determine another value or estimate (e.g., fat fraction) in act 34, which estimate is then used alone, with other types of estimates, with other measurements, or with other types of estimates and other measurements to estimate the disease activity in act 40.

In one embodiment, the backscatter coefficient, acoustic attenuation, and/or shear wave velocity (e.g., using backscatter coefficient (acoustic scattering) and acoustic attenuation without shear wave velocity) are used to estimate the fat fraction in act 34. One or more scattering and/or one or more shear wave propagation parameters are used to estimate fat fraction. Any of the embodiments for estimating fat fraction discussed above for FIG. 1 may be used. For example, the acoustic attenuation coefficient (e.g., a scattering parameter), the backscatter coefficient (e.g., a scattering parameter), and the spectral slope of the logarithm of the frequency-dependent backscatter coefficient (e.g., also a scattering parameter) are used to estimate fat fraction. The shear wave speed (e.g., a shear wave propagation parameter) may be used, such as to select the function for estimating the fat fraction from the scattering parameters.

In act 40, the image processor estimates a level of the liver disease activity (e.g., NAS or UDNA). For indirect estimate, the level of disease activity is estimated from the fat fraction and at least one of the shear wave parameters. For example, three inputs are used in the estimate of disease activity. Ultrasound mechanical and acoustic properties replace histological NAS features. The ultrasound-derived fat fraction, such as based on backscatter, attenuation, and/or sound speed, is used as a measure of steatosis grade. Shear wave damping ratio is used as a measure of inflammation, and shear wave speed is used as a measure of ballooning. The value of the liver disease activity for an index to assist a physician is estimated directly or indirectly from various measurements and/or estimates, such as the fat fraction, the damping ratio, and the shear wave velocity.

Other measurements and/or estimates may be used as replacements. Multiple estimates and/or measurements may be used in place on one histological NAS variable. The activity may be estimated from estimates and/or measurements different than the histological variables, providing a different approach to determining disease activity.

The image processor estimates the score or value for the liver disease activity index using a model. The score or value is part of an index, such as over a range of integers. Any range, such as three levels (e.g., steatohepatitis, cirrhosis, or hepatocellular carcinoma), two levels (e.g., steatosis or fibrosis), or four or more levels, may be used. The scoring may relate to particular stages of disease or may indicate level of disease without reference to particular stages (e.g., 0-7 providing 8 levels with different amounts of activity for each level). The estimated value or score is of a stage and/or numerical representation.

The model may be a function, such as using the estimates and/or measurements in variables. In other embodiments, the model is a machine-learnt classifier. Machine learning, such as using a fully connected neural network, a convolutional neural network, or a support vector machine, trains the model to classify—output the value of the disease activity given the input estimates and/or measurements. In another embodiment, a logistic regression model is used. The value of the disease activity is estimated from the measurements and/or estimates with logistic regression. For example, the disease activity is estimated with a logistic regression of the fat fraction, the shear wave velocity, and the damping ratio. As another example, the disease activity is estimated as a logistic regression of the backscatter coefficient, the shear wave velocity, and the shear wave damping ratio.

The image processor may use other input information to estimate the disease activity. For example, measurements of tissue response to a longitudinal wave from ARFI may be used. As another example, clinical information for the patient may be used.

In act 42, the image processor generates and a display (e.g., display screen) displays the estimate of the disease activity. The level of liver disease activity (e.g., UDNA) is displayed to the user to assist in disease diagnosis or monitoring. Since ultrasound is used, the assistance is provided without invasive biopsy and/or time and expense of MRI.

The level (e.g., value) of the UNDA index or other scale of disease activity is output as alphanumeric text, as a graph, or as color coding or labeling in an image representing tissue of the patient. For example, an ultrasound image of the liver tissue is displayed. The image includes an indication of the value of the ultrasound-derived liver disease activity index as estimated. The fat fraction, other tissue property estimate, and/or measurements may also be output. Any of the outputs discussed above for act 38 may be used with the disease activity instead of or in addition to the fat fraction.

Figure 4:
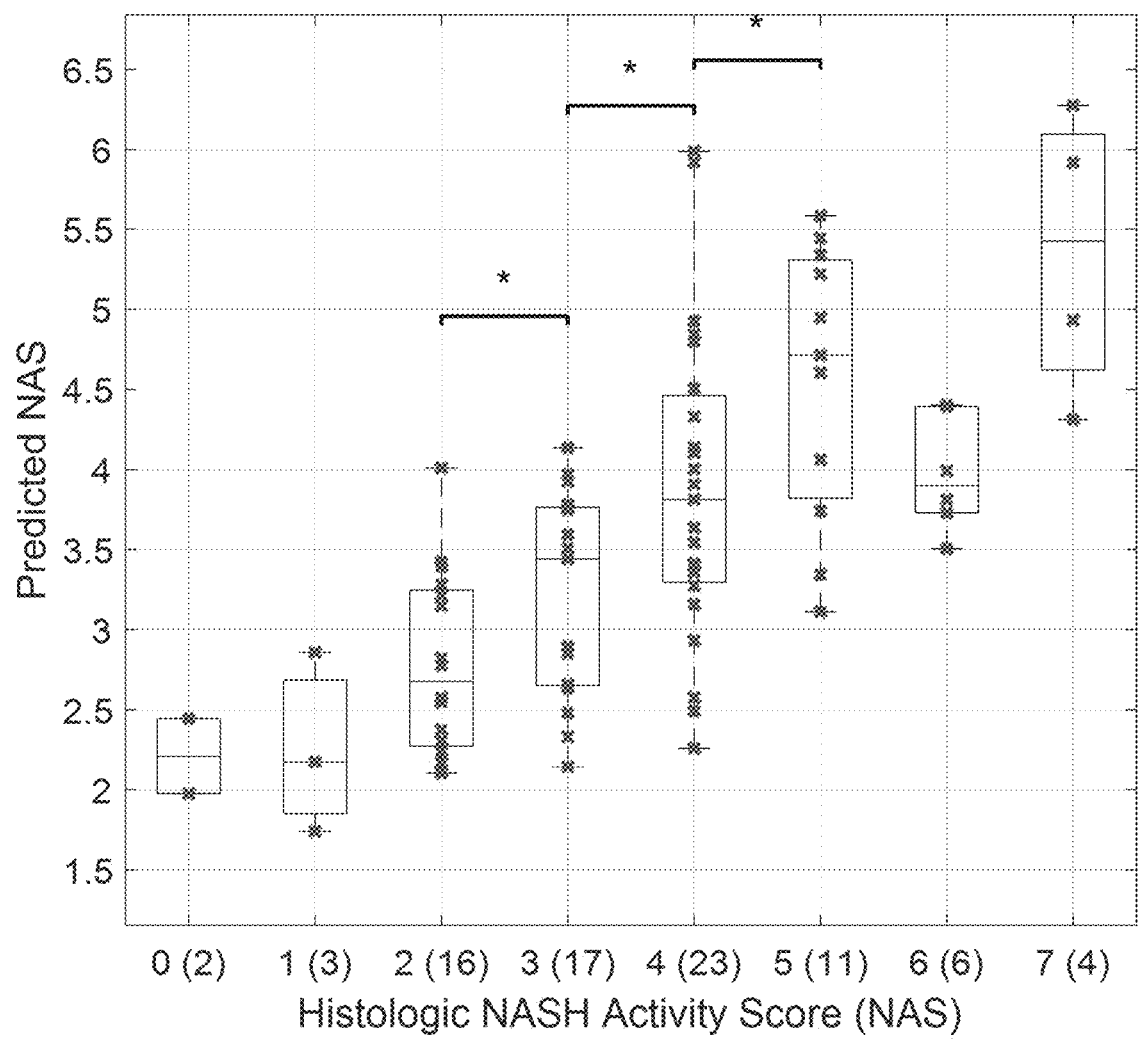
FIG. 4 is an example plot showing accuracy in predicting NAS from ultrasound measures as compared to histologic NAS.

FIG. 4 shows a graph of predicted NAS compared to histologic NAS. The predicted NAS is an estimation of UDNA from logistic regression from fat fraction, shear wave velocity, and shear wave damping ratio based on shear wave propagation. The index uses eight levels for scoring (0-7). Based on 82 patients, the root mean square error between predicted NAS and histologic NAS is 1.14. The predicted correlates well with the histologic NAS, particularly for the mid-range scores of 2-5. Good diagnostic performance is provided.

FIG. 2 shows one embodiment of a system 10 for tissue property and/or disease activity estimation from measures responsive to different types of waves. The system 10 implements the method of FIG. 1, the method of FIG. 3, or other methods. The system 10 includes a transmit beamformer 12, a transducer 14, a receive beamformer 16, an image processor 18, a display 20, and a memory 22. Additional, different or fewer components may be provided. For example, a user input is provided for user interaction with the system.

The system 10 is a medical diagnostic ultrasound imaging system. In alternative embodiments, the system 10 is a personal computer, workstation, PACS station, or other arrangement at a same location or distributed over a network for real-time or post acquisition imaging.

The transmit and receive beamformers 12, 16 form a beamformer used to transmit and receive using the transducer 14. Sequences of pulses are transmitted, and responses received based on operation or configuration of the beamformer. The beamformer scans for measuring scatter, shear wave, and/or ARFI parameters. The beamformers 12, 16 are configured to transmit and receive sequences of pulses in a patient with the transducer 14. The sequence of pulses is for one or more scatter parameters and for one or more shear wave parameters.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated electrical waveforms, one or more beams are formed. A sequence of transmit beams are generated to scan a two or three-dimensional region. Sector, Vector®, linear, or other scan formats may be used. The same region may be scanned multiple times using different scan line angles, F numbers, and/or waveform center frequencies. For flow or Doppler imaging and for shear imaging, a sequence of scans along the same line or lines is used. In Doppler imaging, the sequence may include multiple beams along a same scan line before scanning an adjacent scan line. For shear imaging, scan or frame interleaving may be used (i.e., scan the entire region before scanning again). Line or group of line interleaving may be used. In alternative embodiments, the transmit beamformer 12 generates a plane wave or diverging wave for more rapid scanning.

The same transmit beamformer 12 generates impulse excitations or electrical waveforms for generating acoustic energy to cause displacement. Electrical waveforms for acoustic radiation force impulses are generated. In alternative embodiments, a different transmit beamformer is provided for generating the impulse excitation. The transmit beamformer 12 causes the transducer 14 to generate pushing pulses or acoustic radiation force pulses.

The transducer 14 is an array for generating acoustic energy from electrical waveforms. For an array, relative delays focus the acoustic energy. A given transmit event corresponds to transmission of acoustic energy by different elements at a substantially same time given the delays. The transmit event may provide a pulse of ultrasound energy for displacing the tissue. The pulse may be an impulse excitation, tracking pulse, B-mode pulse, or pulse for other measures. Impulse excitation includes waveforms with many cycles (e.g., 500 cycles) but that occurs in a relatively short time to cause tissue displacement over a longer time. A tracking pulse may be B-mode transmission, such as using 1-5 cycles. The tracking pulses are used to scan a region of a patient.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16. Alternatively, a single element with a mechanical focus is used.

The receive beamformer 16 includes a plurality of channels with amplifiers, delays, and/or phase rotators, and one or more summers. Each channel connects with one or more transducer elements. The receive beamformer 16 is configured by hardware or software to apply relative delays, phases, and/or apodization to form one or more receive beams in response to each imaging or tracking transmission. Receive operation may not occur for echoes from the impulse excitation used to displace tissue. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or another band.

In coordination with the transmit beamformer 12, the receive beamformer 16 generates data representing the region. For tracking a shear wave or axial longitudinal wave, data representing the region at different times is generated. After the acoustic impulse excitation, the receive beamformer 16 generates beams representing locations along one or a plurality of lines at different times. By scanning the region of interest with ultrasound, data (e.g., beamformed samples) is generated. By repeating the scanning, ultrasound data representing the region at different times after the impulse excitation is acquired.

The receive beamformer 16 outputs beam summed data representing spatial locations. Data for a single location, locations along a line, locations for an area, or locations for a volume are output. Dynamic focusing may be provided. The data may be for different purposes. For example, different parts of a scan are performed for B-mode or tissue data than for displacement. Alternatively, the B-mode data is also used to determine displacement. As another example, data for different types of measures are acquired with a series of shared scans, and B-mode or Doppler scanning is performed separately or using some of the same data.

The image processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information for display from beamformed ultrasound samples. In one embodiment, the image processor 18 includes one or more detectors and a separate image processor. The separate image processor is a control processor, general processor, digital signal processor, application specific integrated circuit, field programmable gate array, network, server, group of processors, data path, combinations thereof or other now known or later developed device for calculating values of different types of parameters from beamformed and/or detected ultrasound data and/or for estimating from the values from the different types of measures. For example, the separate image processor is configured by hardware, firmware, and/or software to perform acts 34-38 shown in FIG. 1 and/or acts 34-42 shown in FIG. 3.

The image processor 18 is configured to estimate a value for the tissue property and/or disease activity from a combination of different types of parameters. For example, a measured scatter parameter and one, two, or more measured shear wave parameters are used. The different types of parameters are measured based on the transmit and receive sequences and calculation from the results. The values of the one or more measures of each of at least two of the types (e.g., scatter, shear wave propagation, or axial ARFI) of parameters are determined for fat fraction estimation. The values of one or more scatter and one or more (e.g., two) shear wave propagation parameters are determined for liver disease activity estimation.

In one embodiment, the image processor 18 estimates the tissue property based on the different types of parameters or measures of tissue reaction to different types of wave fronts. The estimation applies a machine-learnt classifier. The input values of the measures with or without other information are used by a learnt matrix to output a value of the tissue property. In other embodiments, the image processor 18 uses a weighted combination of the values of the parameters. For example, two or more functions are provided. Using the value of one or more parameters (e.g., shear wave speed), one of the functions is selected. The selected function uses the values of the same and/or different parameters to determine the value of the tissue property. A linear or non-linear mapping relates values of one or more parameters to the value of the tissue property. For example, two or more scatter parameters are used to determine the value of the tissue property with a shear wave propagation selected function.

In another embodiment, the image processor 18 is configured to generate a score for an index of the disease activity from a combination of one or more scatter parameters and one or more (e.g., two) shear wave parameters. For example, the image processor 18 estimates a fat fraction of a liver of the patient from one or more scatter parameters. The image processor 18 generates the score as an ultrasound-derived non-alcoholic liver disease activity from the fat fraction and two or more shear wave parameters. The score is generated with a machine-learnt classifier or a logistic regression model. For example, the logistic regression model relates the scatter (e.g., acoustic backscatter coefficient) and two or more shear wave parameters (e.g., shear wave velocity and shear wave damping ratio) to the level of disease activity.

The processor 18 is configured to generate one or more images. For example, a shear wave velocity, B-mode, contrast agent, M-mode, flow or color mode, ARFI, and/or another type of image is generated. The shear wave velocity, flow, or ARFI image may be presented alone or as an overlay or region of interest within a B-mode image. The shear wave velocity, flow, or ARFI data modulates the color at locations in the region of interest. Where the shear wave velocity, flow, or ARFI data is below a threshold, B-mode information may be displayed without modulation by the shear wave velocity.

Other information is included in the image or displayed sequentially or substantially simultaneously. For example, a tissue property estimate image and/or disease activity level are displayed at a same time as the other image. A value or values of the tissue property and/or disease activity map may display information. Where the tissue property and/or disease activity are measured at different locations, the values of the tissue property and/or disease activity may be generated as a color overlay in the region of interest in B-mode images. The shear wave velocity, tissue property, and/or disease activity data may be combined as a single overlay on one B-mode image. Alternatively, the value or values of the tissue property and/or disease activity are displayed as text or numerical value(s) adjacent or overlaid on a B-mode or shear wave imaging image. The image processor 18 may be configured to generate other displays. For example, the shear wave velocity image is displayed next to a graph, text, or graphical indicators of the tissue property, such as fat fraction and/or degree of fibrosis, and/or disease activity, such as an index value indicting level of UDNA. The tissue property information and/or disease activity are presented for one or more locations of the region of interest without being in a separate two or three-dimensional representation, such as where the user selects a location and the ultrasound scanner then presents the tissue property and/or disease activity for that location.

The image processor 18 operates pursuant to instructions stored in the memory 22 or another memory for estimation from measures of tissue reaction to different types of waves (e.g., scattering from a transmitted ultrasound, on-axis tissue displacement, and/or a shear wave caused by tissue displacement). The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a device, such as a CRT, LCD, projector, plasma, or other display for displaying one or two-dimensional images or three-dimensional representations. The two-dimensional images represent spatial distribution in an area. The three-dimensional representations are rendered from data representing spatial distribution in a volume. The display 20 is configured by the image processor 18 or other device by input of the signals to be displayed as an image. The display 20 displays an image representing the tissue property and/or disease activity for a single location (e.g., averaged from tissue property estimates including adjacent locations), in a region of interest, or an entire image. For example, the display 20 displays a value for fat fraction and/or a score for an index of disease activity. The display of the tissue property and/or disease activity based on the different types of waves provides more accurate tissue property or level of disease information for diagnosis.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for non-alcoholic liver disease activity estimation with an ultrasound scanner, the method comprising:
   generating a first measure of scattering in tissue from a scan of a patient by the ultrasound scanner, the first measure of scattering comprising a backscatter coefficient;
   generating second and third measures of shear wave propagation in the tissue from the scan of the patient by the ultrasound scanner, the second measure comprising a shear wave velocity and the third measure comprising a shear wave damping ratio;
   estimating a first value for an ultrasound-derived liver disease activity index directly or indirectly as a logistic regression from: (a) a fat fraction derived from the backscatter coefficient and an acoustic attenuation, (b) the shear wave velocity, and (c) the shear wave damping ratio; and
   outputting an ultrasound image including an indication of the first value of the ultrasound-derived liver disease activity index as estimated.

2. The method of claim 1 wherein generating the first, second, and third measures from the scan comprises separate transmit and receive events for (1) the first measure of scattering and (2) the second and third measures of shear wave propagation.

3. The method of claim 1 wherein generating the first measure of scattering comprises generating a frequency-dependent backscatter coefficient as the backscatter coefficient.

4. The method of claim 1 wherein generating the third measure comprises generating the shear wave damping ratio as a ratio of real and imaginary parts of a complex number from a Fourier transformation of spatial-temporal displacements caused by the shear wave propagation.

5. The method of claim 1 wherein generating the third measure comprises generating the shear wave damping ratio from a shear wave attenuation and a shear wave dispersion.

6. The method of claim 1 wherein estimating the first value comprises estimating the fat fraction of a liver of the patient from the acoustic attenuation, the backscatter coefficient, and the shear wave velocity, and estimating, indirectly, the first value for the ultrasound-derived liver disease activity index from the fat fraction, the damping ratio, and the shear wave velocity.

7. The method of claim 6 wherein estimating the first value comprises estimating indirectly with the logistic regression of the fat fraction, the shear wave velocity, and the damping ratio.

8. The method of claim 1 wherein generating the first measure of comprises generating the first measure of as a frequency dependent measure averaged from multiple transmissions.

9. The method of claim 1 wherein generating the first, second, and third measures comprises adaptive scanning.

10. The method of claim 1 wherein estimating comprises estimating as a function of clinical information for the patient.

11. A system for estimation of disease activity, the system comprising:
a transducer;
a beamformer configured to transmit and receive sequences of pulses in a patient with the transducer, the sequence of pulses being for a scatter parameter and for first and second shear wave parameters, the first and second shear wave parameters comprising shear wave velocity and shear wave damping ratio;
an image processor configured to generate a score for an index of the disease activity from a logistic regression based on a combination of: (a) a fat fraction derived from the scatter parameter, the first shear wave parameter, and the second shear wave parameter; and
a display configured to display the score for the index of the disease activity.

12. The system of claim 11 wherein the image processor is configured to generate the score with a machine-learnt classifier.

13. The system of claim 11 wherein the image processor is configured to generate the score with a logistic regression model of the scatter parameter, the first shear wave parameter, and the second shear wave parameter.

14. The system of claim 11 wherein the scatter parameter comprises acoustic backscatter coefficient.

15. The system of claim 11 wherein the image processor is configured to estimate the fat fraction of a liver of the patient from the scatter parameter, and the image processor is configured to generate the score as an ultrasound-derived non-alcoholic liver disease activity from the fat fraction, the first shear wave parameter, and the second shear wave parameter.

16. A method for liver disease activity estimation with an ultrasound system, the method comprising:
determining, by the ultrasound system, one or more scattering parameters of liver tissue of a patient;
determining, by the ultrasound system, a plurality of shear wave parameters of the liver tissue of the patient, the plurality of shear wave parameters comprising shear wave velocity and shear wave damping ratio;
estimating a fat fraction from at least one of the scattering parameters;
estimating a level of the liver disease activity as a logistical regression from the fat fraction the shear wave velocity and the shear wave damping ratio; and
displaying the level of the liver disease activity.

17. The method of claim 16 wherein estimating the fat fraction comprises estimating from an acoustic attenuation and an acoustic scattering as the scattering parameters.

* * * * *